US008911794B2

(12) United States Patent  
Ferrier et al.

(10) Patent No.: US 8,911,794 B2
(45) Date of Patent: Dec. 16, 2014

(54) METHOD OF PRODUCING COPPER HYDROXOSULPHATES AND COPPER FUNGICIDAL COMPOSITIONS CONTAINING SAME

(75) Inventors: Frederic Ferrier, Marseilles (FR); Gerard Joncheray, Vernon (FR); Marc Pillot, Vitrolles (FR)

(73) Assignee: Cerexagri, Plaisir (FR)

( * ) Notice: Subject to any disclaimer, the term of this patent is extended or adjusted under 35 U.S.C. 154(b) by 2041 days.

(21) Appl. No.: 10/552,833

(22) PCT Filed: Apr. 14, 2004

(86) PCT No.: PCT/FR2004/000913  
§ 371 (c)(1),  
(2), (4) Date: Aug. 21, 2006

(87) PCT Pub. No.: WO2004/094315  
PCT Pub. Date: Nov. 4, 2004

(65) Prior Publication Data  
US 2007/0003635 A1 Jan. 4, 2007

(30) Foreign Application Priority Data

Apr. 16, 2003 (FR) ...................... 03 04784

(51) Int. Cl.  
*A01N 59/20* (2006.01)  
*A61K 33/34* (2006.01)  
*C01G 3/00* (2006.01)  
*C01G 3/10* (2006.01)

(52) U.S. Cl.  
CPC .. *C01G 3/00* (2013.01); *C01G 3/10* (2013.01); *A01N 59/20* (2013.01)  
USPC .......................................... 424/633; 424/637

(58) Field of Classification Search  
CPC ................................ A01N 59/20; A61K 33/34  
See application file for complete search history.

(56) References Cited

U.S. PATENT DOCUMENTS

| 2,947,659 | A | * | 8/1960 | Rogers | 424/631 |
| 3,404,951 | A | * | 10/1968 | Tanabe et al. | 423/557 |
| 3,725,535 | A | | 4/1973 | Barker | |
| 4,049,801 | A | * | 9/1977 | Debourge et al. | 514/129 |
| 5,958,438 | A | | 9/1999 | Courtade et al. | |
| 6,375,965 | B1 | * | 4/2002 | Matsuo et al. | 424/405 |
| 6,562,757 | B1 | * | 5/2003 | Ferrier et al. | 504/127 |

FOREIGN PATENT DOCUMENTS

FR 2739256 10/1991

OTHER PUBLICATIONS

Annales de Chimie, vol. 5, pp. 337-405, 1936.  
Encyclopaedia Gmelins Handbuch der Anorganischen Chemie, pp. 579-585, 1958.  
Zeitschrift fur Anorg. Allgem. Chem., pp. 58-65, 1965.  
Encyclopedia of Electrochemistry of the Elements, vol. II, Annex I, Allan J. Bard, 15, 1037 (1974).

* cited by examiner

Primary Examiner — Alton Pryor  
(74) Attorney, Agent, or Firm — John P. White; Cooper & Dunham LLP

(57) ABSTRACT

The subject of the invention is a process for the manufacture of aqueous suspensions of copper hydroxosulphates such as brochantite or antlerite, or a mixture of both, having a high copper content by weight, by reacting an aqueous solution of copper sulphate with an aqueous suspension of copper oxide or copper hydroxide in which the mean diameter of the solid particles is less than 25 μm.

The invention also relates to the preparation of cupric fungicidal compositions having a copper content which may be as high as 45%, in the form of powders, granules or suspension concentrates, dispersible in water, and their use for the fungicidal treatment of crops.

26 Claims, No Drawings

METHOD OF PRODUCING COPPER HYDROXOSULPHATES AND COPPER FUNGICIDAL COMPOSITIONS CONTAINING SAME

The present invention relates to the field of plant-protection products, and its subject is more particularly a process for the manufacture of aqueous suspensions of copper hydroxosulphates such as brochantite and antlerite, or a mixture of both, at a high content by weight of copper, and their use for the preparation of cupric fungicidal compositions in the form of powders, granules or suspension concentrates, which are dispersible in water.

Copper hydroxosulphates represent the active ingredient of Bordeaux mixture. Bordeaux mixture is one of the oldest fungicides used against vine downy mildew. Its use results from the observation by Alexis Millardet, professor at the faculty of Bordeaux, who demonstrated in 1885 the efficacy of this cupric preparation on vine downy mildew (*Plasmopara viticola*).

Currently, Bordeaux mixture occupies an important place among fungicidal cuprate preparations. Its protection against vine downy mildew and its complementary actions such as the limitation of grey mould, powdery mildew, acid rot and bacterial tumours make this cupric preparation a major product for the protection of grape vine. In arboriculture, Bordeaux mixture exhibits efficacies on the apple tree and the pear tree against the European canker, scab and fire blight. On the peach tree and the nectarine, it is used against leaf curl and bacterial withering. The diversity of its uses can also be verified in the case of market gardening crops. There may be mentioned for example its use against downy mildew and bacteriosis of tomato or against angular spot diseases and purple and red spot diseases of strawberry plants. Its efficacy against vine downy mildew, its multiple complementary actions on other phytopathogenic organisms and its low phytotoxicity make Bordeaux mixture one of the most polyvalent fungicides for plant protection.

The fungicidal efficacy of Bordeaux mixture and its lack of phytotoxicity are linked to its multiphase composition of copper complexes (also called copper hydroxosulphates), among which are brochantite of formula $Cu_4(SO_4)(OH)_6$ and antlerite of formula $Cu_3(SO_4)(OH)_4$. These copper hydroxosulphates release, according to slow and steady kinetics, copper(II) ions into the surroundings of the pest, which confers on Bordeaux mixture a fungicidal activity unmatched by the other fungicidal cupric forms such as copper hydroxide or copper oxychloride, and an optimum efficacy—lack of phytotoxicity balance.

There is however a major disadvantage in the use of Bordeaux mixture, which stems from the quantity of products used by the user. Indeed, a conventional Bordeaux mixture consists, in addition to a mixture of copper hydroxosulphates, of a multiphase mixture of calcium complexes, by-products inherent to its synthesis carried out starting with copper sulphate and lime.

These by-products can represent more than 50% of the formula and consist mainly of gypsum and bassanite.

Improvements in the process for the manufacture of Bordeaux mixture have been made in order to obtain a formula in which the copper is in the form of brochantite and in which the content of bassanite in the formula in the dry state is limited to 20%; these improvements were the subject of Patent FR 2 739 256.

However, in the case of this optimized Bordeaux mixture, the content by weight of active ingredient represented by the copper(II) ion does not exceed 27.3%. Consequently, the copper content of Bordeaux mixture compositions cannot exceed 25% by weight and generally has a value of 20% by weight, unlike the other cupric formulations, based on copper hydroxide or copper oxychloride, in which the copper content may be as high as 40% or even 50% by weight. This is due to the fact that the copper hydroxide or copper oxychloride cupric forms possess 65% and 58% by weight of copper(II) ion, respectively. Considering the approved dose of 2.4 kg of copper per hectare, it is evident that a treatment with a Bordeaux mixture composition is carried out with 12 kg of formulated product whereas the specialities with higher copper titres allow the use of lower quantities of formulated product, 6 kg or even 4.8 kg of formulated product.

Other routes which are conventionally used for the manufacture of hydroxosulphates are the neutralization of copper sulphate solutions with sodium hydroxide or potassium hydroxide. These processes make it possible, after extensive washing of the precipitated products, to obtain copper hydroxosulphates in which the copper content of the solids is greater than 48%. However, the washing phase provides large quantities of effluent loaded with sodium or potassium sulphate. This type of process cannot therefore be envisaged industrially.

Brochantite and antlerite can also be obtained from the reaction of copper(II) oxide with copper sulphate according to the following equations:

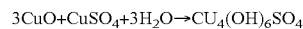

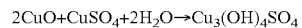

These reactions are already described in the literature. There may be mentioned Encyclopaedia of Electrochemistry of the elements—Vol II—Allen J. Bard where the standard potentials of the oxidation-reduction reactions with copper oxides are given.

O. Binder, in Annales de Chimie, volume 5, 336 (1936), studies the production of basic copper salts by the action of aqueous solutions of copper sulphate or of sulphuric acid on divalent copper oxide or hydroxide using the method of solubility isotherms and the method of residues. The existence of basic salts (another name for copper hydroxosulphates), demonstrated by these two methods, was confirmed by the study of the X-ray diffraction spectra. These studies demonstrate the formation of antlerite when the reaction temperature is 100° C. and the formation at 22° C. of the copper salt $SO_3$, $4CuO$, $4H_2O$ which, by dehydration at 150° C., leads to brochantite.

These same studies are described and detailed by E. H. Erich Pietsch in the encyclopaedia Gmelins Handbuch der Anorganischen Chemie, 1958, Verlag Chemie, pages 579-535.

In patent U.S. Pat. No. 3,725,535, it is mentioned that the preparation of basic copper sulphates from copper oxide CuO and copper sulphate is difficult and slow.

The publication Denk, Leschhorn, Z. Anorg. Allgem. Chem. 336, 58 (1965) describes the reactivity between copper hydroxide and copper sulphate. It is specified that the oxide CuO can be used in the same manner as copper hydroxide. Operating conditions are given (molar ratios, temperature) and the conditions for using the reagents (concentration, order of introduction of the reagents and the like), but these conditions do not allow total reactivity of the copper oxide and the concentrations of the copper hydroxosulphate suspensions obtained are too low to envisage industrial development.

There has now been found a novel process for the manufacture of copper hydroxosulphates such as brochantite or antlerite or a mixture of both, by reacting an aqueous solution of copper sulphate $CuSO_4$ with an aqueous suspension of copper oxide or copper hydroxide, which has the advantage of limiting the quantity of by-products formed (gypsum, sodium or potassium sulphate) and of leading to suspensions in which the content by weight of solids is greater than 10%; furthermore, the content by weight of copper of the solid phase, consisting of at least 85% of copper hydroxosulphates, is greater than 48%.

The subject of the invention is therefore first a process for the manufacture of aqueous suspensions of brochantite ($Cu_4(OH)_6SO_4$) or antlerite ($Cu_3(OH)_4SO_4$) or a mixture of both, having a content by weight of solids greater than 10%, by reacting an aqueous solution of copper sulphate $CuSO_4$ with an aqueous suspension of copper oxide or copper hydroxide used in a total $SO_4/CU$ molar ratio ranging from 0.25 to 0.40, the said process being characterized in that an aqueous solution of $CuSO_4$ having a concentration by weight of copper of between 6% and 10% is mixed with an aqueous suspension of copper oxide or copper hydroxide having a concentration of between 15% and 50% by weight and in which the mean diameter of the solid particles is less than 25 μm, the reaction being carried out at a controlled temperature of between 40° C. and 100° C.

Unless otherwise stated in the description, the percentages expressed represent percentages by weight.

The subject of the invention is also a process for the preparation of cupric fungicidal compositions demanded by the market from aqueous suspensions of brochantite or antlerite or a mixture of the two thus obtained, and also the cupric fungicidal compositions as prepared according to this process:

- Bordeaux mixture enriched with copper as sole fungicide, which has a copper content of between 30 and 45%,
- combination of this copper-enriched Bordeaux mixture with at least one synthetic fungicide, which leads to a copper content of between 15% and 40%, preferably between 18% and 40%, according to the following presentations:

- WP (wettable powder) type formulation dispersible in water,
- WG (water-dispersible granule) type formulation with a higher apparent particle size distribution (of the order of 50 to 400 μm), dispersible in water, releasing little or no dust at the time of use,
- SC (suspension concentrate) type liquid formulation dispersible in water.

The aqueous suspensions of copper hydroxosulphates such as brochantite or antlerite or a mixture of both are obtained according to the process of the invention from an aqueous solution of copper sulphate and an aqueous suspension of copper oxide or copper hydroxide which are used in an $SO_4/Cu$, where Cu represents the number of moles of copper in all forms, molar ratio of between 0.25 and 0.40.

The copper content by weight of the aqueous solution of copper sulphate introduced into the reaction medium may vary between 6% and 10%. However, it is preferable to use an aqueous solution of copper sulphate in which the copper content is between 6.5% and 8%, and more particularly between 6.6% and 7.6%.

The aqueous suspension of copper oxide or copper hydroxide used in the process has a concentration of between 15% and 50% by weight, preferably between 20% and 30% by weight. The diameter of the particles of the aqueous suspension of copper oxide or copper hydroxide is a critical parameter which determines the good process of the reaction. Grinding is generally carried out under conditions known to a person skilled in the art in order to significantly increase the specific surface area of these suspensions and thus their reactivity. It will be sought to obtain, for the aqueous suspension of copper oxide or copper hydroxide, a particle size distribution in which the mean diameter of the solid particles is less than 25 μm, preferably of between 0.1 and 10 μm and more particularly between 0.5 and 5 μm, and in which the wet sieving residue at 25 μm relative to the dry extract is less than 5% by weight, and more particularly less than 2% by weight (according to the CIPAC MT 59.3 method). The grinding of copper oxide or copper hydroxide in suspension may be optionally carried out in the presence of copper sulphate. The presence of copper sulphate in the aqueous suspension of copper oxide or copper hydroxide makes it possible to optimize the grinding of copper oxide in acid medium, and consequently to increase its reactivity.

The aqueous solution of copper sulphate and the aqueous suspension of copper oxide or copper hydroxide which are described above are mixed in the process according to the invention after having heated one or both of them beforehand to an initial temperature at most equal to 100° C. The order of addition of the reagents is not a critical parameter for the obtaining of brochantite, but for the exclusive obtaining of antlerite, it is necessary for the aqueous suspension of copper oxide or copper hydroxide to be added to the aqueous solution of copper sulphate heated beforehand to an initial temperature at most equal to 100° C.

It has also been found that a sulphuric acid solution may be used instead of the aqueous copper sulphate solution. In this case, the solubilization of the copper oxide or of the copper hydroxide in the acid medium leads in situ to the formation of copper sulphate. Thus, the presence of residual sulphuric acid $H_2SO_4$ as impurity inherent to the manufacture of copper sulphate from copper and sulphuric acid is not a limiting factor for the reaction used in the process of the invention. The concentration of residual sulphuric acid may be between 0 and 1% by weight.

According to a first variant embodiment of the process according to the invention, the initial temperature of the reaction medium is less than or equal to 60° C., preferably between 40° C. and 60° C.; the initial temperature of the reaction medium is maintained for a period of between one hour and 3 hours, and then the reaction medium is brought to a higher temperature which is maintained for at least one hour. The higher temperature to which the reaction medium is brought is at most equal to 100° C., preferably between 65° C. and 80° C. This variant is preferred, because it is suitable for the manufacture of aqueous suspensions of brochantite having a solids content by weight greater than 10%. When the reaction medium is brought to a higher temperature, the reaction can lead to an increase in viscosity which can limit the homogenization of the suspension. In order to preserve good homogeneity of the mixture and good progress of the reaction, dilution by addition of water may be carried out in order to reduce the level of dry matter in the mixture. There is used according to this first variant an aqueous solution of copper sulphate and an aqueous suspension of copper oxide or hydroxide with a total $SO_4/Cu$ molar ratio ranging from 0.25 to 0.34.

According to a second variant embodiment of the process according to the invention, the initial temperature of the reaction medium is between 70° C. and 100° C., preferably between 80° C. and 90° C. This temperature is maintained for a period of between 0.5 hour and 3 hours. There is used according to this second variant an aqueous solution of copper sulphate and an aqueous suspension of copper oxide or hydroxide in a total $SO_4/Cu$ molar ratio ranging from 0.33 to 0.40. According to this embodiment, for the exclusive obtaining of antlerite, it is necessary for the aqueous suspension of copper oxide or copper hydroxide to be added to the aqueous solution of copper sulphate brought beforehand to the initial temperature.

At the end of the reaction, the excess copper sulphate is separated by filtration or neutralized. The neutralization of the excess copper sulphate may be carried out with any organic or inorganic base. As examples of organic bases, there may be mentioned the salts of carboxylic or polycarboxylic acids in which the cation may be sodium, potassium or ammonium. As other examples of organic bases, amines may be mentioned. As examples of inorganic bases, there may be mentioned sodium hydroxide, potassium hydroxide, lime, aqueous ammonia, sodium or potassium carbonate.

The reaction product exists in the form of an aqueous suspension in which the solid content by weight is greater than 10% and in which the copper content by weight of the solid phase, consisting of at least 85% of copper hydroxosulphates, is greater than 48%. The content by weight of the suspension may be increased by a concentration (centrifugation or decantation) step. The paste thus obtained may be used for the manufacture of SC (suspension concentrate), SE (suspo-emulsion) or WG (water-dispersible granule) type fungicidal formulations dispersible in water and stable during storage.

For the manufacture of a WP-type wettable powder, the paste obtained after concentration needs to be dried. The paste may be dried with the aid of any type of drier known to persons skilled in the art in order to obtain a powder having a titre of less than 1% moisture. An advantageous alternative consists in fluidifying the paste with any chemical agent known to persons skilled in the art. The fluidized paste can then be spray-dried.

The invention also relates to a process for the preparation of cupric fungicidal compositions demanded by the market, using aqueous suspensions of brochantite or antlerite or a mixture of both, prepared according to the process described above, in the form of a fluidized paste or a powder, used as sole fungicides or in combination with other fungicidal synthetic organic substances.

The manufacture of the cupric fungicidal compositions is carried out in a manner known per se, using the customary adjuvants (dispersants, wetting agents, anti-foaming agents, colorants, thickeners, inert fillers, pH regulator). The fungicidal synthetic organic substances are chosen from in particular compounds whose F-ISO common names are mancozeb, maneb, zineb, cymoxanil, famoxadone, benthiavalicarb. Cupric fungicidal formulations are obtained according to the invention having a copper content of between 30 and 45%, or between 15% and 40%, preferably between 18 and 40%, according to whether the copper hydroxosulphates are sole fungicides or combined with other active ingredients.

In the following examples which illustrate the invention without limiting it, the percentages are understood by weight unless otherwise stated.

EXAMPLE 1

Grinding of a Copper(II) Oxide Suspension

Into a stirred reactor, there were introduced 19 800 g of water and then 6600 g of technical copper(II) oxide having a copper content equal to 78% and in which the mean diameter of the particles is of the order of 35 μm. The mixture is pumped into a ball mill of the Dyno mill KDL pilot type having a working volume of 1.4 liters. Recycling is performed at a high flow rate (about 50 l/h) for 30 minutes so as to rapidly refine the particle size distribution of the copper(II) oxide. At the end of the recycling, the particle size of the copper(II) oxide reaches 3 to 4 μm. A run is then made at a flow rate of 20 to 30 l/h so as to reach a final particle size of the order of 2 μm. The particle size characteristics of the copper(II) oxide thus ground, measured on a granulometer of the MALVERN mastersizer 2000 type are:

Mean diameter of the particles=2 μm
Percentage of particles whose diameter is >6 μm=10%
Percentage of particles whose diameter is >10 μm=5%
Percentage of particles whose diameter is >25 μm=0.5%
Wet sieving residue at 25 μm of the solid particles of the copper(II) oxide suspension (CIPAC MT 59.3 method)=0.5% (expressed relative to the suspension dry extract)

EXAMPLE 2

Manufacture of Brochantite

Into a stirred reactor, there were introduced 11 330 g of solution of copper sulphate having a copper content equal to 7.08% and containing 0.2% of sulphuric acid. The solution is heated to 50° C., and then 9500 g of suspension of copper(II) oxide (CuO) finely ground according to Example 1 and having a content by weight equal to 25% are added. The mixture is kept at 50° C. for 1 h 30 min during which the colour of the suspension changes from black to grey. After 1 h 30 min reaction, the temperature is raised to 70° C. 6330 g of water are added while heating. The formation of brochantite is marked by the passage from the grey colour to the green colour. The end of the reaction is reached while keeping the mixture at 70° C., with stirring for 1 h. At the end of the reaction, the content by weight of solids of the brochantite suspension is 17%. The reaction mixture is then added to a milk of lime composed of 140 g of lime and 900 ml of water. One hour after the addition of the reaction mixture to the milk of lime, the mixture was filtered and about 11000 g of paste were obtained containing 44.1% of dry extract of which a portion was dried in an oven. The characteristics of the solid thus obtained are the following:

Copper content by weight: 50.8%
Water content<1%
pH at 1% in distilled water: 5.9
X-ray analysis shows that this solid is composed of brochantite and gypsum.

EXAMPLE 3

Manufacture of Antlerite

In a stirred reactor, there were introduced 9770 g of solution of copper sulphate at 7.16% of Cu containing 0.2% of sulphuric acid. The solution is heated to 90° C. and then 7300 g of suspension of technical copper(II) oxide (CuO) ground according to Example 1 and having a dry matter content equal to 24.36% are added. The addition of the copper(II) oxide suspension is carried out over 20 min. At the end of the addition, the colour of the suspension becomes green. The suspension is kept between 85 and 95° C. for 30 min. At the end of the reaction, an antlerite suspension is obtained in which the solids content by weight is 22.4%. The mixture was then filtered and a paste was obtained of which a portion was dried and analysed. The powder obtained has the following characteristics:

Copper content by weight: 51.6%
Water content<1%
pH at 1% in distilled water: 5.5
Analysis by infrared spectroscopy shows that this solid is composed of antlerite.

EXAMPLE 4

Production of a Fluidized Paste of Brochantite

Into a stirred tank, there were introduced 11000 g of paste obtained according to Example 2, and then 220 g of sodium polynaphthalenesulphonate (dispersing agent). After stirring, a fluidized paste was obtained which, after wet grinding, was used for the manufacture of formulations of the SC or WG type. The physical characteristics of this fluid paste are the following:
Solids: 45.2%
Copper content by weight: 22.0%
Particle size: 2 μm

EXAMPLE 5

Production of a Fluidized Paste of Antlerite

Into a stirred tank, there were introduced 7000 g of paste obtained according to Example 3, and then 140 g of sodium polynaphthalenesulphonate (dispersing agent). After stirring, a fluidized paste was obtained which, after wet grinding, was used for the manufacture of formulations of the SC or WG type. The physical characteristics of this fluid paste are the following:
Solids: 50.7%
Copper content by weight: 25.2%
Particle size: 1.6 μm

EXAMPLE 6

Production of Water-Dispersible Brochantite Granules

Into a tank equipped with a stirrer, there were successively introduced 3700 g of fluidized paste obtained according to Example 4 (solids=45.2%, % Cu=22.0%), and then 59.8 g of polynaphthalenesulphonate, 160 g of lignosulphonate, 67 g of a premixture containing 30% of Prussian blue and 55 g of gypsum. The suspension was then sent into a drying tower and granules were thus obtained containing 40% of copper, easily dispersible in water and having the following characteristics (CIPAC methods):
Wet residue 45 μm: <1%
Suspendability: >75%
Foam: <20 ml

EXAMPLE 7

Production of Water-Dispersible Antlerite Granules

Into a tank equipped with a stirrer, there were successively introduced 6600 g of fluidized paste obtained according to Example 5 (solids=50.72%, % Cu=25.15%), and then 143 g of polynaphthalenesulphonate, 322 g of lignosulphonate and 151 g of gypsum. The suspension was then sent into a drying tower and granules were thus obtained containing 42% of copper, easily dispersible in water and having the following characteristics (CIPAC methods):
Wet residue 45 μm: <1%
Suspendability: >75%
Foam: <20 ml

EXAMPLE 8

Production of Water-Dispersible Brochantite and Benthiavalicarb Granules

Into a tank equipped with a stirrer, there were successively introduced 2550 g of fluidized paste obtained according to Example 4 (solids=45.2%, % Cu=22.0%), and then 49.2 g of polynaphthalenesulphonate, 120 g of lignosulphonate, 7.5 g of alkyl naphthalenesulphonate, 3 g of citric acid monohydrate, 3 g of an antifoam based on acetylenic diol, 50 g of a premixture containing 30% of Prussian blue, 72.3 g of gypsum and 52.5 g of a premixture containing 50% of benthiavalicarb. The suspension was then sent into a drying tower and granules were thus obtained containing 37.5% of copper and 1.75% of benthiavalicarb, easily dispersible in water and having the following characteristics (CIPAC methods):
Wet residue 45 μm: <1%
Suspendability: >75%
Foam: <20 ml

EXAMPLE 9

Production of Water-Dispersible Brochantite and Mancozeb Granules

Into a tank equipped with a stirrer, there were successively introduced 1900 g of fluidized paste obtained according to Example 4 (solids=45.2%, % Cu=22.0%), and then 582 g of water, 305 g of polynaphthalenesulphonate, 101 g of a premixture containing 30% of Prussian blue, 97 g of kaolin and 1258 g of mancozeb having a purity greater than 85%. The suspension was then sent into a drying tower and granules were thus obtained containing 16% of copper and 40% of mancozeb, easily dispersible in water and having the following characteristics (CIPAC methods):
Wet residue 45 μm: <1%
Suspendability: >75%
Foam: <20 ml

EXAMPLE 10

Production of Water-Dispersible Brochantite Granules Containing 20% of Copper

Into a tank equipped with a stirrer, there were successively introduced 2806 g of fluidized paste obtained according to Example 4 (solids=45.2%, % Cu=22.0%), and then 840 g of water, 350 g of polynaphthalenesulphonate, 101 g of a premixture containing 30% of Prussian blue, 1153 g of gypsum and 182 g of kaolin. The suspension was then sent into a drying tower and granules were thus obtained containing 20.7% of copper, easily dispersible in water and having the following characteristics (CIPAC methods):
Wet residue 45 μm: <1%
Suspendability: >75%
Foam: <20 ml

EXAMPLE 11

Biological Trials

In the context of controlling vine downy mildew, comparative treatment trials were carried out between the commercial Bordeaux mixture with the reference BBRSR Disperss and a copper-enriched Bordeaux mixture composition obtained according to Example 6 of the invention. The trials were carried out on fruit carrying vine plants according to the CEB method No. 7 (trials under misting with artificial contamination).

The efficacy of the treatment is determined by evaluating, on the one hand, the percentage of vine leaves affected by downy mildew and the percentage of leaf surface area destroyed, and on the other hand, the percentage of grape bunches affected and the percentage of harvest destroyed.

The results of the 10 scores awarded are assembled in Table 1 (scores on leaf) and Table 2 (scores on grape bunches).

They show that the composition according to Example 6, used at the dose of 6 kg/ha, is as effective as the Bordeaux mixture BBRSR Disperss used at a dose of 12 kg/ha.

TABLE 1

Scores on leaves

| Composition | Cu content of the composition | Dose of copper per hectare (kg) | Quantity of composition per hectare (kg) | % of leaves affected | | | % of leaf surface destroyed | | |
|---|---|---|---|---|---|---|---|---|---|
| | | | | 1 | 2 | 3 | 4 | 5 | 6 |
| BBRSR Disperss | 20% | 2.4 | 12 | 47.0 | 37.0 | 29.3 | 5.3 | 4.6 | 3.4 |
| Example 6 | 40% | 2.4 | 6 | 39.0 | 29.0 | 25.8 | 4.2 | 4.3 | 3.5 |
| % attack on control | 0 | 0 | 0 | 66.0 | 72.0 | 84.5 | 10.2 | 15.2 | 33.7 |

TABLE 2

Scores on grape bunches

| Composition | Cu content of the composition | Dose of copper per hectare (kg) | Quantity of composition per hectare (kg) | % of grape bunches affected | | % of harvest destroyed | |
|---|---|---|---|---|---|---|---|
| | | | | 7 | 8 | 9 | 10 |
| BBRSR Disperss | 20% | 2.4 | 12 | 50.5 | 58.0 | 5.0 | 9.8 |
| Example 6 | 40% | 2.4 | 6 | 42.0 | 53.0 | 5.5 | 6.0 |
| % attack on control | 0 | 0 | 0 | 83.0 | 87.5 | 22.8 | 28.9 |

The invention claimed is:

1. A hydroxosulfate mixture of both brochantite ($Cu_4(OH)_6 SO_4$) and antlerite ($Cu_3(OH)_4SO_4$), wherein the copper content of the mixture attributable to brochantite and antlerite is between 30% and 45% by weight of the mixture, wherein the mixture is made by a process which comprises reacting an aqueous solution of copper sulphate ($CuSO_4$) with an aqueous suspension of solid particles of copper oxide in a total $SO_4/Cu$ molar ratio ranging from 0.25 to 0.40, the aqueous solution of $CuSO_4$ having a concentration by weight of copper of between 6% and 10% and the aqueous suspension of solid particles of copper oxide having a concentration of copper oxide between 15% and 50% by weight wherein the mean diameter of the solid particles of copper oxide in the suspension is less than 25 μm, and wherein the reaction is carried out at a controlled temperature between 40° C. and 100° C.

2. A cupric fungicidal composition comprising the hydroxosulfate mixture of claim 1 and a synthetic fungicide, wherein the copper content of the cupric fungicidal composition attributable to the mixture of brochantite and antlerite is between 18% and 40% by weight of the composition.

3. The cupric fungicidal composition of claim 2, wherein the synthetic fungicide is selected from the group consisting of mancozeb, maneb, zineb, cymoxanil, famoxadone, and benthiavalicarb.

4. The hydroxosulfates mixture of claim 1, wherein the hydroxosulfates mixture is in the form of a suspension concentrate, suspo-emulsion, dispersable granule, or wettable powder.

5. The hydroxosulfates mixture of claim 1 further comprising one or more adjuvants selected from the group consisting of dispersing agents, wetting agents, antifoaming agents, colorants, thickeners, pH regulators, and fillers.

6. A process for the manufacture of the hydroxosulfates mixture of claim 1 which comprises reacting an aqueous solution of copper sulphate ($CuSO_4$) with an aqueous suspension of solid particles of copper oxide in a total $SO_4/Cu$ molar ratio ranging from 0.25 to 0.40, the aqueous solution of $CuSO_4$ having a concentration by weight of copper of between 6% and 10% and the aqueous suspension of solid particles of copper oxide having a concentration of copper oxide between 15% and 50% by weight wherein the mean diameter of the solid particles of copper oxide in the suspension is less than 25 μm, and wherein the reaction is carried out at a controlled temperature between 40° C. and 100° C.

7. The process according to claim 6, wherein the aqueous suspension of solid particles of copper oxide additionally contains copper sulphate.

8. The process according to claim 6, wherein the mean diameter of the solid particles of copper oxide in the aqueous suspension is between 0.1 and 10 μm.

9. The process according to claim 6, wherein in that a residue from wet sieving with a 25 μm sieve of the solid particles in the aqueous suspension of copper oxide relative to a dry extract of the solid particles in the aqueous suspension of copper oxide is less than 5% by weight.

10. The process according to claim 6, wherein the aqueous solution of $CuSO_4$ has a copper concentration by weight between 6.5% and 8%.

11. The process according to claim 6, wherein the aqueous suspension of copper oxide has a concentration between 20% and 30% by weight.

12. The process according to claim 6, wherein the copper oxide is copper(II) oxide CuO.

13. The process according to claim 6, wherein at end of the reaction, excess copper sulphate is removed by filtration or neutralized with aid of an organic or inorganic base.

14. The process according to claim 13, wherein the organic base is a salt of carboxylic or polycarboxylic acid in which the cation is selected from the group consisting of a sodium ion, a potassium ion, an ammonium ion, and an amine.

15. The process of claim 6, wherein the total $SO_4$/Cu molar ratio ranges from 0.25 to 0.34, wherein the reaction is carried out at an initial temperature less than or equal to 60° C. for between one hour and 3 hours, and wherein the reaction is thereafter carried out at a higher temperature for at least one hour.

16. The process according to claim 15, wherein the initial temperature is between 40° C. and 60° C.

17. The process according to claim 15, wherein the higher temperature is at most equal to 100° C.

18. The process of claim 6, wherein the total $SO_4$/Cu molar ratio ranges from 0.33 to 0.40, and wherein a reaction medium is kept at an initial temperature of at most equal to 100° C. for between 0.5 hour and 3 hours.

19. The process according to claim 18, wherein the initial temperature is between 70° C. and 100° C.

20. A method for fungicidal treatment of a crop in need of fungicidal treatment, comprising administering an effective amount of the hydroxosulfates mixture of claim 1 to the crop.

21. The process according to claim 6, wherein the mean diameter of the solid particles of copper oxide in the aqueous suspension is between 0.5 and 5 μm.

22. The process according to claim 6, wherein a residue from wet sieving with a 25 μm sieve of the solid particles in the aqueous suspension of copper oxide relative to a dry extract of the solid particles in the aqueous suspension of copper oxide is less than 2% by weight.

23. The process according to claim 6, wherein the aqueous solution of $CuSO_4$ has a copper concentration by weight between 6.6% and 7.6%.

24. The process according to claim 13, wherein neutralization of excess copper sulphate is carried out with the aid of an inorganic base selected from the group consisting of sodium hydroxide, potassium hydroxide, lime, aqueous ammonia, sodium carbonate, and potassium carbonate.

25. The process according to claim 15, wherein the higher temperature is between 65° C. and 80° C.

26. The process according to claim 18, wherein the initial temperature is between 80° C. and 90° C.

* * * * *